(12) United States Patent
Ishimaru et al.

(10) Patent No.: US 10,004,391 B2
(45) Date of Patent: Jun. 26, 2018

(54) ELECTRONIC ENDOSCOPE DEVICE HAVING TEMPERATURE CONTROL

(71) Applicant: FUJIFILM Corporation, Tokyo (JP)

(72) Inventors: Yoshiaki Ishimaru, Ashigarakami-gun (JP); Mitsuru Higuchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 918 days.

(21) Appl. No.: 14/498,432

(22) Filed: Sep. 26, 2014

(65) Prior Publication Data

US 2015/0094531 A1 Apr. 2, 2015

(30) Foreign Application Priority Data

Sep. 27, 2013 (JP) ................................. 2013-201910

(51) Int. Cl.
*A61B 1/045* (2006.01)
*A61B 1/05* (2006.01)
(Continued)

(52) U.S. Cl.
CPC .............. *A61B 1/128* (2013.01); *A61B 1/045* (2013.01); *A61B 1/05* (2013.01); *A61B 1/0661* (2013.01); *H04N 2005/2255* (2013.01)

(58) Field of Classification Search
CPC ........... A61B 1/05; A61B 1/045; A61B 1/128; A61B 1/0661; H04N 5/2256; H04N 2005/2255
See application file for complete search history.

(56) References Cited

U.S. PATENT DOCUMENTS 6,464,633 B1 * 10/2002 Hosoda ................ A61B 1/0638
348/68
6,796,939 B1 * 9/2004 Hirata ................ A61B 1/00036
600/109
(Continued)

FOREIGN PATENT DOCUMENTS

JP 63-185380 U 11/1988
JP 2000-278677 A 10/2000
(Continued)

OTHER PUBLICATIONS

Japanese Office Action and partial English translation thereof, dated Dec. 8, 2015, for Japanese Application No. 2013-201910.
(Continued)

*Primary Examiner* — John P Leubecker
(74) *Attorney, Agent, or Firm* — Birch, Stewart, Kolasch & Birch, LLP

(57) ABSTRACT

An electronic endoscopic device includes a light source, an endoscopic scope including an imaging unit provided at a tip end, a temperature detecting unit that detects a temperature of the tip end, and a light source control unit that performs a light emission control and a light emission stop control in a frame period. The imaging unit includes a plurality of pixels and a driving unit, and the electronic endoscopic device further includes a control unit in which, when a temperature detected by the temperature detecting unit exceeds a threshold value, the control unit performs a control such that, in a frame period following a first frame period, a period in which the light emission stop control is performed is set to be longer, and a read-out speed of the imaging signal is set to be slower.

8 Claims, 2 Drawing Sheets

(51) Int. Cl.
*A61B 1/12* (2006.01)
*A61B 1/06* (2006.01)
*H04N 5/225* (2006.01)

(56) References Cited

U.S. PATENT DOCUMENTS

| | | | |
|---|---|---|---|
| 6,798,456 B1 * | 9/2004 | Sato | H04N 5/2353 348/244 |
| 2002/0013512 A1 * | 1/2002 | Sendai | A61B 5/0071 600/160 |
| 2003/0043263 A1 | 3/2003 | Glukhovsky et al. | |
| 2003/0128285 A1 * | 7/2003 | Itoh | H04N 5/361 348/246 |
| 2005/0159643 A1 | 7/2005 | Zinaty et al. | |
| 2005/0182291 A1 * | 8/2005 | Hirata | A61B 1/00096 600/101 |
| 2005/0187433 A1 | 8/2005 | Horn et al. | |
| 2007/0112247 A1 * | 5/2007 | Hirata | A61B 1/0607 600/101 |
| 2007/0225560 A1 * | 9/2007 | Avni | A61B 1/00006 600/118 |
| 2008/0036856 A1 | 2/2008 | Yamada et al. | |
| 2008/0058602 A1 | 3/2008 | Landry | |
| 2012/0016201 A1 * | 1/2012 | Seto | A61B 1/045 600/180 |
| 2012/0035419 A1 * | 2/2012 | Ashida | A61B 1/00009 600/109 |
| 2012/0038801 A1 * | 2/2012 | Yamada | H04N 5/3458 348/278 |
| 2012/0116157 A1 * | 5/2012 | Seto | A61B 1/00057 600/109 |
| 2012/0123213 A1 * | 5/2012 | Seto | A61B 1/0638 600/178 |
| 2012/0127338 A1 * | 5/2012 | Suzuki | H04N 5/361 348/229.1 |
| 2012/0226102 A1 * | 9/2012 | Kagaya | A61B 1/045 600/109 |
| 2012/0308082 A1 * | 12/2012 | Murao | G06K 9/00825 382/103 |
| 2013/0016200 A1 * | 1/2013 | Ovod | A61B 1/06 348/68 |
| 2013/0030248 A1 * | 1/2013 | Matsumaru | A61B 1/00027 600/110 |
| 2013/0033625 A1 * | 2/2013 | Kato | H04N 5/361 348/244 |
| 2013/0035545 A1 * | 2/2013 | Ono | A61B 1/045 600/109 |
| 2013/0169775 A1 * | 7/2013 | Ono | A61B 1/00009 348/68 |
| 2013/0308019 A1 * | 11/2013 | Fukuoka | H04N 5/361 348/243 |
| 2014/0036051 A1 * | 2/2014 | Saito | A61B 1/045 348/68 |
| 2014/0052004 A1 * | 2/2014 | D'Alfonso | A61B 1/0669 600/476 |
| 2014/0307071 A1 * | 10/2014 | Hirosawa | A61B 1/00133 348/65 |

FOREIGN PATENT DOCUMENTS

| | | |
|---|---|---|
| JP | 2008-36220 A | 2/2008 |
| JP | 2008-80112 A | 4/2008 |
| JP | 2008-535547 A | 9/2008 |
| JP | 2009-178180 A | 8/2009 |
| JP | 2011-250926 A | 12/2011 |
| JP | 2012-81001 A | 4/2012 |
| JP | 2012-100834 A | 5/2012 |
| JP | 2012-143319 A | 8/2012 |
| JP | 2013-466 A | 1/2013 |
| WO | WO 2013/128764 A1 | 9/2013 |

OTHER PUBLICATIONS

Japanese Notification of Reasons for Refusal, dated Aug. 9, 2016, for Japanese Application No. 2013-201910, including an English machine translation.

* cited by examiner

ELECTRONIC ENDOSCOPE DEVICE HAVING TEMPERATURE CONTROL

CROSS-REFERENCE TO RELATED APPLICATIONS

This application is based on and claims priority under 35 USC 119 from Japanese Patent Application No. 2013-201910 filed on Sep. 27, 2013, the entire content of which is incorporated herein by reference.

BACKGROUND

1. Technical Field

The present invention relates to an electronic endoscopic device.

2. Related Art

An electronic endoscopic system which is used in a medical field is configured by an electronic endoscope (scope) and a processor device. The electronic endoscope includes an imaging device including a solid-state imaging element at a tip end of an insertion unit which is inserted into a subject. The processor device controls an operation of the imaging device and performs various signal processings on an imaging signal which is output from the imaging device to display an endoscopic image on a monitor (a display device).

The temperature inside the tip end of the endoscope insertion unit easily rises due to, for example, heat generation of the solid-state imaging element (a CCD sensor or a CMOS sensor) or heat generation from lost light quantity of a light guide. When an internal temperature of the endoscope insertion unit rises, a noise of an image signal is increased and an image quality is degraded. Further, when a temperature of the tip end of the endoscope insertion unit exceeds a reference temperature, a safety problem may be caused. Therefore, it is demanded to take preventive measures to detect a temperature of the endoscope insertion unit to control the temperature or issue a warning to an operator of the endoscope when the temperature rises.

Patent Literature 1 (JP-A-2013-000466) discloses a configuration which includes a temperature detecting unit at a tip end of an endoscope insertion unit so that when the detected temperature of the tip end becomes high, a frame rate is decreased and a light quantity is reduced to suppress heat generation.

Patent Literature 2 (JP-A-2012-143319) discloses a configuration which includes a temperature detecting unit at a tip end of an endoscope insertion unit so that when the detected temperature of the tip end becomes high, a frame rate is decreased to suppress heat generation.

Patent Literature 3 (JP-A-2012-081001) discloses an electronic endoscope which decreases a frame rate to reduce heat generation when a light quantity radiated from the light source exceeds a limit light quantity.

SUMMARY OF INVENTION

As disclosed in Patent Literatures 1 to 3, according to the configuration in which the frame rate is decreased to suppress the heat generation in the tip end of the endoscope insertion unit, since the frame rate varies during the imaging, it is difficult to synchronize with a display system and as a result an unnatural moving image may be displayed.

An illustrative aspect of the present invention is to provide an electronic endoscopic device which may provide a moving image to be displayed which does not give a feeling of strangeness even when the temperature of the tip end of the endoscope insertion unit rises.

An aspect of the present invention provides an electronic endoscopic device including: a light source that generates light to be irradiated onto a portion to be observed; an endoscopic scope including an imaging unit provided at a tip end of the endoscopic scope, the imaging unit capturing the portion to be observed; a temperature detecting unit that detects a temperature of the tip end; and a light source control unit that performs a light emission control to intermittently or continuously emit the light from the light source in a part of a frame period and perform a light emission stop control to continuously stop emitting the light from the light source in a remaining part of the frame period, the frame period being a period for obtaining one frame of a moving image by the imaging unit, in which the imaging unit includes a plurality of pixels which is arranged two-dimensionally and a driving unit which performs driving to read out an imaging signal from the plurality of pixels, in a period where the light emission stop control is performed in the frame period, the driving unit performs driving to read out the imaging signal according to charges accumulated in the plurality of pixels, from the plurality of pixels which is exposed during a period where the light emission control is performed in the frame period, and the electronic endoscopic device further includes a control unit in which, when a temperature detected by the temperature detecting unit exceeds a threshold value, the control unit performs, while fixing a length of the frame period, a control such that, in a frame period following a first frame period including a timing at which the temperature exceeding the threshold value is detected, a period in which the light emission stop control is performed is set to be longer than the period in which the light emission stop control is performed in the first frame period, and a read-out speed of the imaging signal from the plurality of pixels by the driving unit is set to be slower than a read-out speed in the first frame period.

According to the electronic endoscope device, it is possible to provide an electronic endoscopic device which may provide a moving image to be displayed which does not give a feeling of strangeness even when the temperature of the tip end of the endoscope insertion unit rises.

DESCRIPTION OF EMBODIMENTS

Hereinafter, an exemplary embodiment of the present invention will be described with reference to the drawings.

Figure 1:
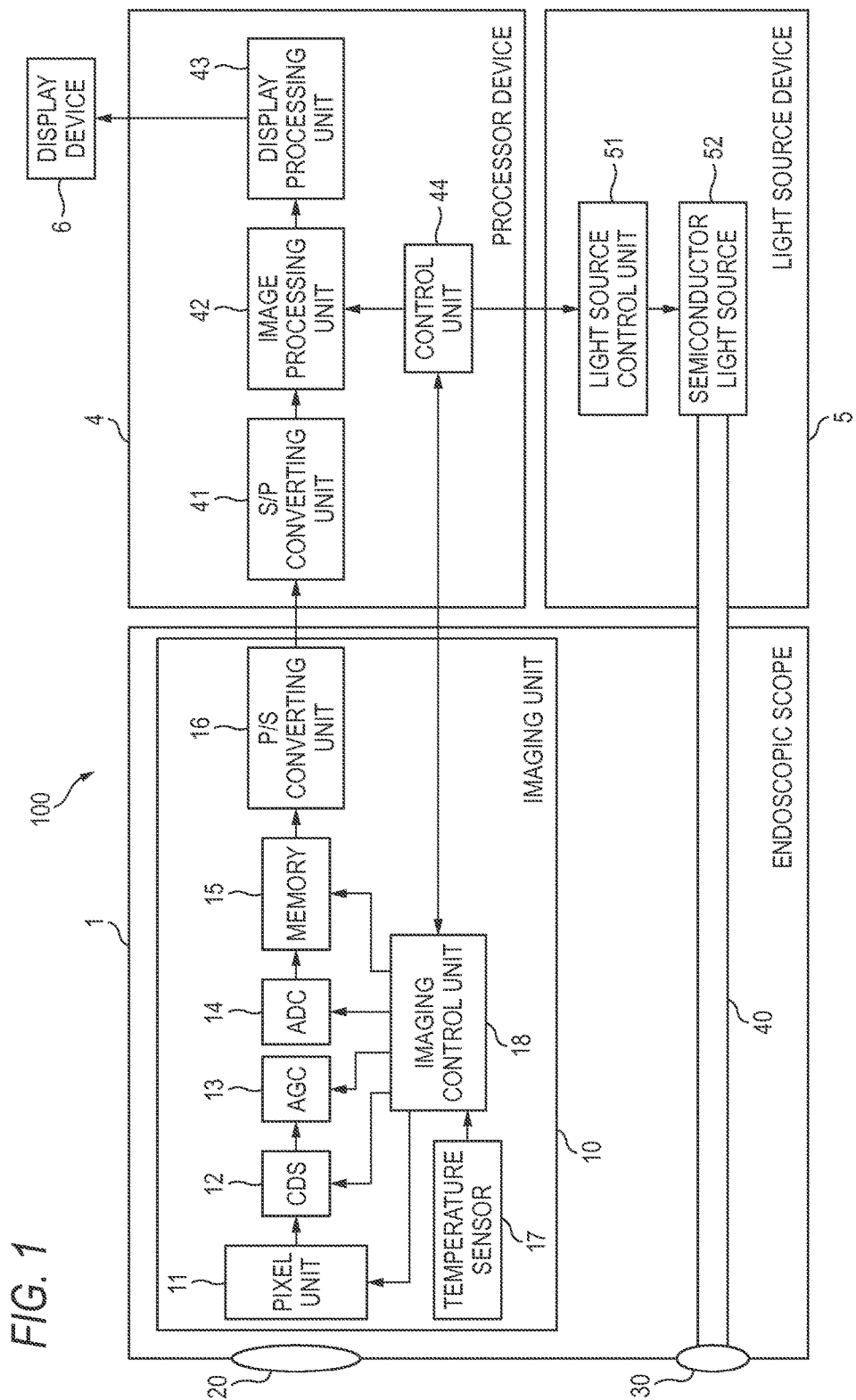
FIG. 1 is a view illustrating a schematic configuration of an electronic endoscopic device 100 according to an exemplary embodiment of the present invention.

FIG. 1 is a view illustrating a schematic configuration of an electronic endoscopic device 100 according to an exemplary embodiment of the present invention.

The electronic endoscopic device 100 includes an endoscopic scope 1, a light source device 5, and a processor device (control device) 4. The endoscope insertion unit 1, the light source device 5, and a display device 6 are electrically connected to the processor device 4 by a cable.

The endoscopic scope 1 includes a flexible endoscope insertion unit which is inserted into a body cavity of a patient (subject) and an operating unit which is provided to be connected to a base end of the endoscope insertion unit.

FIG. 1 illustrates a tip end of the endoscope insertion unit as a part of the endoscopic scope 1. The tip end of the endoscope insertion unit is equipped with an imaging optical system 20 configured to capture an image of a portion to be observed, an imaging unit 10 configured to capture the image of the portion to be observed through the imaging optical system 20, an illumination window 30 configured to illuminate the portion to be observed, and a light guide 40 configured to guide light to the illumination window 30.

The imaging unit 10 includes a pixel unit 11, a CDS 12, an AGC 13, an ADC 14, a memory 15, a P/S converting unit 16, a temperature sensor 17, and an imaging control unit 18.

The pixel unit 11 includes a plurality of pixels which is two-dimensionally arranged. Each pixel includes a photoelectric converting unit such as a photodiode and an MOS circuit which reads out an imaging signal according to charges accumulated in the photoelectric converting unit.

The CDS 12 performs a correlated-double sampling processing on the imaging signal which is read out by each pixel of the pixel unit 11.

The AGC 13 serves as an amplifying unit which multiplies the imaging signal which is processed by the CDS 12 by a gain to amplify the imaging signal.

The ADC 14 converts the imaging signal which is amplified by the AGC 13 into a digital signal having a predetermined bit number.

The memory 15 temporally stores the imaging signal which is converted into the digital signal by the ADC 14. As the memory 15, a storing device (FIFO (first-in first-out) is used. The storing device has a function which firstly extracts data which is previously stored, that is, subsequently extracts data in the order from the oldest data among the stored data when the stored data is extracted.

The P/S converting unit 16 converts the imaging signal stored in the memory 15 into a serial signal and transmits the serial signal to the processor device 4 through a serial line which is embedded in the cable which connects the endoscopic scope 1 and the processor device 4. The P/S converting unit 16 serves as a transmitting unit which sequentially reads out an imaging signal in the order from the oldest one of the imaging signals stored in the memory 15 and transmits the read-out imaging signal to the processor device 4.

The temperature sensor 17 is a temperature detecting unit configured to detect a temperature of the tip end of the insertion unit of the endoscopic scope 1, and for example, may employ a thermal diode.

The imaging control unit 18 collectively controls the whole of the imaging unit 10. The imaging control unit 18 also serves as a driving unit which drives to read out the imaging signal from each pixel of the pixel unit 11.

The imaging control unit 18 is connected to a control unit 44 of the processor device 4 by the serial line which is embedded in the cable which connects the endoscopic scope 1 and the processor device 4. The imaging control unit 18 controls individual units of the imaging unit 10 in accordance with a command from the control unit 44. Further, the imaging control unit 18 transmits temperature information detected by the temperature sensor 17 to the control unit 44.

The imaging unit 10 is configured such that the individual units as described above are integrated in one chip. Recently, due to the increased integration degree, it becomes important to take a measure against temperature rise of the tip end of the endoscope insertion unit, the temperature rise being caused by the heat generated when the imaging unit 10 operates. As long as the temperature sensor 17 is capable of detecting the temperature of the tip end of the endoscope insertion unit, the temperature sensor 17 may not be embedded in the imaging unit 10. However, in the integrated imaging unit 10, since the heat generation in the chip of the imaging unit 10 is large, it is desirable to provide the temperature sensor 17 in the chip.

The light source device 5 includes a light source control unit 51 and a semiconductor light source 52.

The semiconductor light source 52 is a light source configured to generate light to be irradiated to the portion to be observed and the light emitted from the semiconductor light source 52 is introduced in to the light guide 40 and irradiated onto the portion to be observed through the illumination window 30.

The light source control unit 51 performs light emission control by which light is continuously emitted from the semiconductor light source 52 for a predetermined time during a part of a frame period, and light emission stop control by which light emission from the semiconductor light source 52 is continuously stopped for a predetermined time during the remaining frame period. The frame period is a period when one frame of a moving image is obtained when the moving image is captured by the imaging unit 10.

In the light emission control, the semiconductor light source 52 may not be continuously turned on, but may be turned on in pulsed manner so as to intermittently emit light from the semiconductor light source 52 for a predetermined time.

The processor device 4 includes an S/P converting unit 41, an image processing unit 42, a display processing unit 43, and a control unit 44.

The S/P converting unit 41 receives the serial signal transmitted from the P/S converting unit 16 of the endoscopic scope 1 through the serial line and converts the serial signal into a parallel signal.

The image processing unit 42 includes a memory embedded therein. The memory primarily stores the imaging signal which is converted by the S/P converting unit 41. The image processing unit 42 performs an image processing on the imaging signal for one frame of the moving image stored in the memory to generate captured image data.

The display processing unit 43 generates display data from the captured image data generated by the image processing unit 42 and displays an image based on the display data on the display device 6.

The control unit 44 is connected to the imaging control unit 18 of the endoscopic scope 1 and the light source control unit 51 of the light source device 5 by a serial line. The control unit 44 variably controls the light emission period and the light emission stop period of the light source by the light source control unit 51 or variably controls a read-out speed of the imaging signal from the pixel unit 11 of the endoscopic scope 1 based on the detected temperature information of the temperature sensor 17 which is transmitted from the imaging control unit 18 of the endoscopic scope 1. The read-out speed of the imaging signal refers to a number of imaging signals which are output from the pixel unit 11 per unit time.

Figure 2:
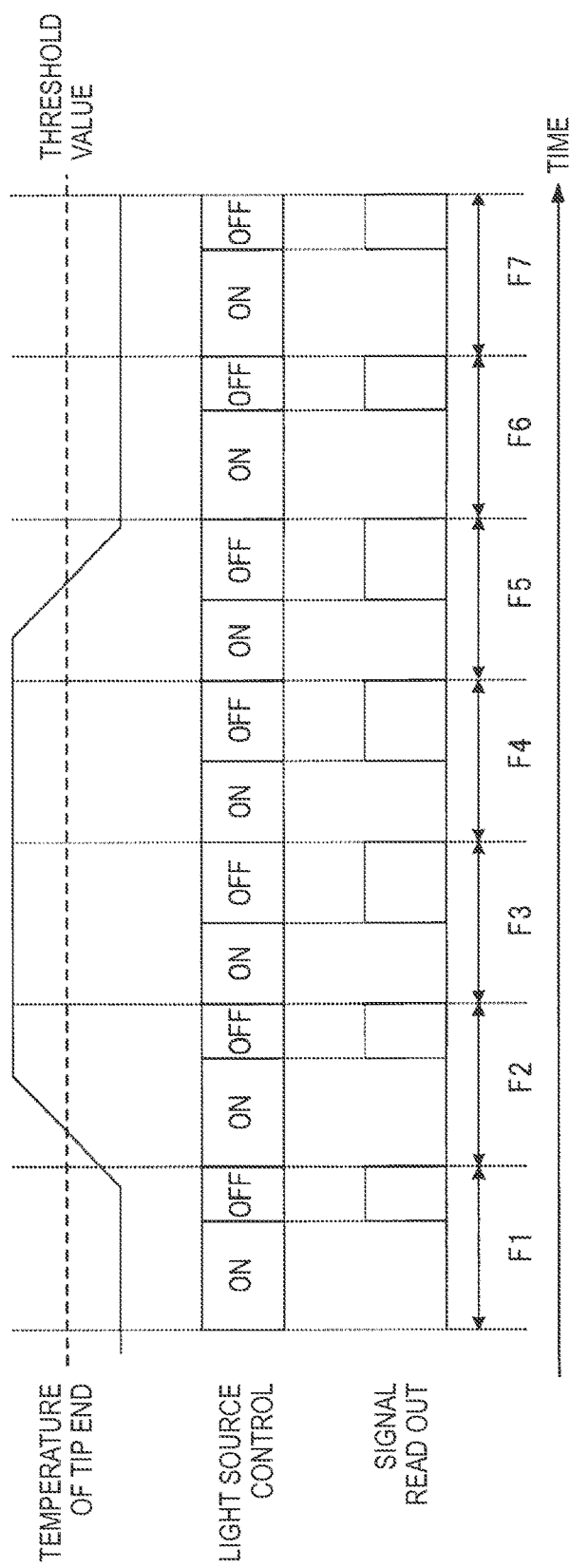
FIG. 2 is a timing chart illustrating an operation when a moving image is captured by an imaging unit 10 of an endoscopic scope 1.

FIG. 2 is a timing chart illustrating an operation when a moving image is captured by the imaging unit 10 of the endoscopic scope 1.

Reference symbols F1 to F7 of FIG. 2 denote frame periods, and a length of each frame period is constantly controlled by the control unit 44 while the moving image is captured.

In FIG. 2, a period denoted by "ON" indicates a period when the light emission control is performed (hereinafter, also referred to as an ON period) and a period denoted by "OFF" indicates a period when the light emission stop control is performed (hereinafter, also referred to as an OFF period). Further, even during the ON period, the light may not be continuously emitted, but may be intermittently emitted.

As illustrated in FIG. 2, in the electronic endoscopic device 100, during the OFF period in each frame period, the imaging control unit 18 is driven to read out the imaging signal according to the charges accumulated in each pixel from the pixel unit 11 which is exposed during the ON period in the frame period.

In an example of FIG. 2, in the middle of a frame period F2, the temperature detected by the temperature sensor 17 exceeds a threshold value. In this case, the control unit 44 performs a control so that during frame periods (F3, F4, and F5 in the example of FIG. 2) following the frame period F2 which includes a timing at which the temperature exceeding the threshold value is detected, an ON period is set to be shorter than an ON period in the frame period F2 and an OFF period is set to be longer than an OFF period in the frame period F2. Further, the control unit 44 performs a control so that the read-out speed of the imaging signal from the plurality of pixels by the imaging control unit 18 is set to be slower than the read-out speed in the frame period F2.

A method of slowing down the read-out speed of the imaging signal includes a thinning method of thinning out a part of the plurality of pixels included in the pixel unit 11 to read out the imaging signal so that a read-out clock is lowered. Alternatively, there is a pixel addition method of adding respective charges accumulated in the plurality of pixels in the unit of the plurality of pixels and reading out the imaging signal according to the sum of charges to lower the read-out clock. Alternatively, there is a method of further lowering the read-out clock while performing the thinning method or the pixel addition method. Further, there is a method of only lowering the read-out clock without changing the number of imaging signals to be read out.

It is required to set the read-out speed of the imaging signal such that the time required for completely reading out the imaging signal for one frame from the pixel unit 11 is equal to or shorter than a length of the OFF period so as not to read out imaging signals during the exposure. The ADC 14 operates in synchronization with the read-out clock of the imaging signal so that a driving frequency is lowered as the read-out clock is lowered, thereby reducing the heat generation.

During the frame periods F3, F4, and F5, since a time when the semiconductor light source 52 is turned off is longer than that in the frame period F2, the tip end of the endoscope insertion unit is suppressed from generating heat caused by light emission from the light guide 40 and the decrease of a temperature at the tip end is accelerated. Further, during the frame periods F3, F4, and F5, since the read-out speed of the imaging signal is slower than that in the frame period F2, the heat generation of the imaging unit 10 is suppressed and the decrease of a temperature at the tip end of the endoscope insertion unit is accelerated.

In the middle of the frame period F5, when the temperature detected by the temperature sensor 17 is equal to or lower than the threshold value, the control unit 44 performs a control so that during a frame period F6 following the frame period F5 which includes a timing at which the temperature not higher than the threshold value is detected, an ON period is set to be longer than the ON period in the frame period F5 (to be equal to the ON period of the frame period F2 in the example of FIG. 2). Further, the control unit 44 performs a control so that the read-out speed of the imaging signal from the plurality of pixels by the imaging control unit 18 during the frame period F6 is set to be faster than the read-out speed during the frame period F5 (to be equal to the read-out speed in the frame period F2 in FIG. 2).

As described above, according to the electronic endoscopic device 100, when the temperature at the tip end portion of the endoscope insertion unit exceeds the threshold value, the OFF period which occupies the frame period becomes longer and the read-out speed of the imaging signal is slower. Thus, the temperature at the tip end may be lowered by reducing the heat generation by stopping the light emission for a long time and decreasing the read-out speed of the imaging signal.

Therefore, the safety of the subject may be secured, and also a thermal noise in the pixels of the pixel unit 11 may be suppressed so that the captured image quality is prevented from being lowered. Further, the temperature rise at the tip end may be suppressed while fixing the length of the frame period so that a captured image without feeling of strangeness may be provided.

The electronic endoscopic device 100 uses FIFO as the memory 15 so that even when the read-out speed of the imaging signal is changed, the imaging signal may be transmitted from the imaging unit 10 to the processor device 4 at a constant speed. Therefore, it is possible to suppress the temperature rise at the tip end and improve the captured image quality without changing the processing at the processor device 4 side.

In the description of FIG. 2, ratios of the ON period and the OFF period which occupy the frame period and the read-out speed of the imaging signal vary in two stages, but may vary in multiple stages.

For example, during the frame period F3, the OFF period is set to be longest and the read-out speed is set to be slowest, and then as the temperature value detected by the temperature sensor 17 is decreased, the OFF period is gradually shortened as compared with the frame period F3 and the read-out speed is gradually sped up as compared with the frame period F3. Finally, both the OFF period and the read-out speed are set to be equal to those in the frame period F2. Accordingly, a change in brightness between adjacent frames may be reduced so that a moving image without a feeling of strangeness may be provided.

During the frame periods F3, F4, and F5, when the imaging signal is read out by a method other than the pixel addition method, the ON period is shortened and thus a brightness level of the imaging signal is lowered. As a result, brightness of the image obtained in the frame periods F1, F2, F6, and F7 is different from brightness of the image obtained in the frame periods F3, F4, and F5.

Accordingly, the control unit 44 issues an instruction to the imaging control unit 18 in the periods F3, F4, and F5 such that a gain is set by the AGC 13 to be larger than a gain in the frame period F2. As described above, the brightness of the captured image obtained in the frame periods F3, F4, and F5 may be set to be equal to the brightness of the captured image obtained in the frame periods F1, F2, F6, and F7 by variably controlling the gain in accordance with the temperature at the tip end so that it is possible to provide a moving image without a feeling of strangeness.

When the gain is variably controlled as described above, in the frame periods F3, F4, and F5, as the gain is increased, the noise included in the captured image is also increased as compared with the noise in the frame period F2. However, in the frame periods F3, F4, and F5, the ON period is shortened and the read-out speed is slowed down so that the decrease of the temperature at the tip end is accelerated. Therefore, the noise increase caused by the gain-up may be compensated by reducing the thermal noise by the decrease of the temperature at the tip end and thus the influence of the noise increase on the image quality is limited.

However, in actuality, until the temperature at the tip end starts decreasing after the frame period F3 following the frame period F2 starts, a little time lag may be generated.

Therefore, in consideration of the time lag, for example, the gain-up may be not performed during the frame period F3 immediately after the frame period F2 but may be performed in the frame periods F4 and F5. According to this method, since the brightness of the captured image obtained during the frame period F3 becomes dark, for example, the pixel addition method may be performed only during the frame period F3 so as not to lower the brightness of the captured image.

In consideration of the time lag and lots of thermal noise which is generated in the pixels when the temperature at the tip end is high, for example, in each of the frame periods F3, F4, and F5, the gain may be set according to the temperature at the tip end immediately before the corresponding frame period is started. Specifically, as the temperature at the tip end immediately before the frame period is started is higher, the gain may be set to be lower.

The exemplary embodiment as described above may be appropriately changed without departing from the technical spirit of the present invention.

For example, although the light source which is mounted in the light source device 5 in FIG. 1 is the semiconductor device 52, a light source which is capable of switching between light emission and light non-emission with high precision may be used. Further, as the imaging unit 10, a CMOS type image sensor in which a signal read-out circuit is provided for every pixel is employed, but the CCD image sensor may be employed therefor. Further, the temperature sensor 17 may not directly detect the temperature. For example, as disclosed in Patent Literature 1, a frequency-temperature characteristic of a quartz resonator which is disposed at the tip end to generate a driving signal may be used to detect the temperature of the tip end. Further, the gain may be controlled not only by the AGC 13 but also by the image processing unit 42.

As described above, the specification discloses the following matters.

An electronic endoscopic device according to the present invention includes: a light source that generates light to be irradiated onto a portion to be observed; an endoscopic scope including an imaging unit provided at a tip end of the endoscopic scope, the imaging unit capturing the portion to be observed; a temperature detecting unit that detects a temperature of the tip end; and a light source control unit that performs a light emission control to intermittently or continuously emit the light from the light source in a part of a frame period, which is a period for obtaining one frame of a moving image by the imaging unit, and perform a light emission stop control to continuously stop emitting the light from the light source in a remaining part of the frame period. The imaging unit includes a plurality of pixels which is arranged two-dimensionally and a driving unit which performs driving to read out an imaging signal from the plurality of pixels. In a period where the light emission stop control is performed in the frame period, the driving unit performs driving to read out the imaging signal according to charges accumulated in the plurality of pixels, from the plurality of pixels which is exposed during a period where the light emission control is performed in the frame period. The electronic endoscopic device further includes a control unit in which, when a temperature detected by the temperature detecting unit exceeds a threshold value, the control unit performs, while fixing a length of the frame period, a control such that, in a frame period following a first frame period including a timing at which the temperature exceeding the threshold value is detected, a period in which the light emission stop control is performed is set to be longer than the period in which the light emission stop control is performed in the first frame period, and a read-out speed of the imaging signal from the plurality of pixels by the driving unit is set to be slower than a read-out speed in the first frame period.

With this configuration, when the temperature at the tip end exceeds the threshold value, a period of the light emission stop control in the frame period is increased and the read-out speed of the imaging signal becomes slower so that the temperature of the tip end may be lowered by reducing the heat generation by stopping the light emission for a long time and decreasing the read-out speed of the imaging signal. Further, the temperature rise at the tip end is suppressed while fixing the length of the frame period so that a captured image quality may not give a feeling of strangeness.

The electronic endoscopic device according to the present invention includes: an amplifying unit that multiplies the imaging signal read out from the plurality of pixels by a gain to amplify the imaging signal. In the frame period in which the period in which the light emission stop control is performed is set to be longer than the period in which the light emission stop control is performed in the first frame period, the amplifying unit sets a gain, which is multiplied by the imaging signal read out from the plurality of pixels, to be larger than a gain, which is multiplied by the imaging signal read out from the plurality of pixels in the first frame period.

With this configuration, a reduced exposure amount of the respective pixels due to an elongation of the period of the light emission stop control may be supplemented with gain-up so that it is possible to prevent the feeling of strangeness from occurring due to a significant momentary change in the brightness of a displayed moving image.

In the electronic endoscopic device according to the present invention, in the frame period in which the period in which the light emission stop control is performed is set to be longer than the period in which the light emission stop control is performed in the first frame period, the amplifying unit sets the gain, which is multiplied by the imaging signal read out from the plurality of pixels, to be lower as the temperature of the tip end immediately before the frame period becomes higher.

With this configuration, in a situation where the temperature of the tip end is high and lots of thermal noises are generated, the gain is set to be low so that the noise of the captured image is reduced, thereby improving a captured image quality.

In the electronic endoscopic device according to the present invention, in the frame period in which the period in which the light emission stop control is performed is set to be longer than the period in which the light emission stop control is performed in the first frame period, the driving unit performs driving to add the charges accumulated in ones of the plurality of pixels in the unit of the ones of the plurality of pixels, and reads out the imaging signal according to the added charges.

With this configuration, a reduced exposure amount of the respective pixels due to an elongation of the period of the light emission stop control may be supplemented with addition of charges of the plurality of pixels so that it is possible to prevent the feeling of strangeness from occurring due to a significant momentary change in the brightness of a captured moving image. Further, the reduced exposure amount is supplemented with the charge addition so that it is possible to prevent an S/N ratio of the imaging signal from being lowered. Further, the number of imaging signals to be read out is reduced by adding the charges so that the read-out speed of the imaging signal becomes slow and the temperature rise of the tip end may be suppressed.

In the electronic endoscopic device according to the present invention, when the temperature detected by the temperature detecting unit becomes equal to or lower than the threshold value from the temperature exceeding the threshold value, the control unit performs a control such that, in a frame period following a second frame period including a timing at which the temperature not greater than the threshold value is detected, a period in which the light emission stop control is performed is set to be shorter than the period in which the light emission stop control is performed in the second frame period and a read-out speed of the imaging signal from the plurality of pixels by the driving unit is set to be higher than a read-out speed in the second frame period.

With this configuration, when the temperature of the tip end is equal to or lower than the threshold value, the length of the period of the light emission stop control in the frame period returns to an original length and the read-out speed of the imaging signal returns to an original speed so that the original status in which the temperature of the tip end does not exceed the threshold value may be maintained.

In the electronic endoscopic device according to the present invention, the endoscopic scope includes: a storing unit that temporally stores the imaging signal read out by the driving unit from the plurality of pixels, and a transmitting unit that reads out the imaging signal stored in the storing unit and transmits the read-out imaging signal to a control device which processes the imaging signal to generate image data. The transmitting unit transmits the imaging signal at a constant transmitting speed regardless of the read-out speed of the imaging signal.

With this configuration, the imaging signal is transmitted from the endoscope insertion unit to the control device at a constant speed so that there is no need to change processing contents of the control device, thereby preventing the cost from being increased.

What is claimed is:

1. An electronic endoscopic device comprising:
   a light source that generates light to be irradiated onto a portion to be observed;
   an endoscopic scope including an imaging unit provided at a tip end of the endoscopic scope, the imaging unit capturing the portion to be observed;
   a temperature detecting unit that detects a temperature of the tip end; and
   a light source control unit that performs a light emission control to intermittently or continuously emit the light from the light source in a part of a frame period and perform a light emission stop control to continuously stop emitting the light from the light source in a remaining part of the frame period, the frame period being a period for obtaining one frame of a moving image by the imaging unit, wherein
   the imaging unit includes a plurality of pixels which is arranged two-dimensionally and a driving unit which performs driving to read out an imaging signal from the plurality of pixels,
   in a period where the light emission stop control is performed in the frame period, the driving unit performs driving to read out the imaging signal according to charges accumulated in the plurality of pixels, from the plurality of pixels which is exposed during a period where the light emission control is performed in the frame period,
   the electronic endoscopic device further comprises a control unit in which, when a temperature detected by the temperature detecting unit exceeds a threshold value, the control unit performs, while fixing a length of the frame period, a control such that, in a frame period following a first frame period including a timing at which the temperature exceeding the threshold value is detected, a period in which the light emission stop control is performed is set to be longer than the period in which the light emission stop control is performed in the first frame period, and a read-out speed of the imaging signal from the plurality of pixels by the driving unit is set to be slower than a read-out speed in the first frame period,
   the control unit slows down the read-out speed by lowering a read-out clock without changing a number of imaging signals read out by the driving unit in the first frame period and a number of imaging signals read out by the driving unit in a frame period following the first frame period,
   the electronic endoscopic device further comprises an amplifying unit that multiplies the imaging signal read out from the plurality of pixels by a gain to amplify the imaging signal, and
   the amplifying unit sets a gain, which is multiplied by the imaging signal read out from the plurality of pixels in a third frame period in the frame period in which the period in which the light emission stop control is performed is set to be longer than the period in which the light emission stop control is performed in the first frame period, except for the frame period immediately after the first frame period to be larger than a gain, which is multiplied by the imaging signal read out from the plurality of pixels in the first frame period, and sets the gain, which is multiplied by the imaging signal read out from the plurality of pixels in the frame period immediately after, to be equal to the gain which is multiplied by the imaging signal read out from the plurality of pixels in the first frame period.

2. The electronic endoscopic device of claim 1, wherein, in the third frame period, the amplifying unit sets the gain, which is multiplied by the imaging signal read out from the plurality of pixels, to be lower as the temperature of the tip end immediately before the third frame period becomes higher.

3. The electronic endoscopic device of claim 2, wherein, when the temperature detected by the temperature detecting unit becomes equal to or lower than the threshold value from the temperature exceeding the threshold value, the control unit performs a control such that, in a frame period following a second frame period including a timing at which the temperature not greater than the threshold value is detected, a period in which the light emission stop control is performed is set to be shorter than the period in which the light emission stop control is performed in the second frame period and a read-out speed of the imaging signal from the plurality of pixels by the driving unit is set to be higher than a read-out speed in the second frame period.

4. The electronic endoscopic device of claim 3, wherein the endoscopic scope includes: a storing unit that temporally stores the imaging signal read out by the driving unit from the plurality of pixels, and a transmitting unit that reads out the imaging signal stored in the storing unit and transmits the read-out imaging signal to a control device which processes the imaging signal to generate image data, and the transmitting unit transmits the imaging signal at a constant transmitting speed regardless of the read-out speed of the imaging signal.

5. The electronic endoscopic device of claim 2, wherein the endoscopic scope includes: a storing unit that temporally stores the imaging signal read out by the driving unit from the plurality of pixels, and a transmitting unit that reads out the imaging signal stored in the storing unit and transmits the read-out imaging signal to a control device which processes the imaging signal to generate image data, and the transmitting unit transmits the imaging signal at a constant transmitting speed regardless of the read-out speed of the imaging signal.

6. The electronic endoscopic device of claim 1, wherein, when the temperature detected by the temperature detecting unit becomes equal to or lower than the threshold value from the temperature exceeding the threshold value, the control unit performs a control such that, in a frame period following a second frame period including a timing at which the temperature not greater than the threshold value is detected, a period in which the light emission stop control is performed is set to be shorter than the period in which the light emission stop control is performed in the second frame period and a read-out speed of the imaging signal from the plurality of pixels by the driving unit is set to be higher than a read-out speed in the second frame period.

7. The electronic endoscopic device of claim 6, wherein the endoscopic scope includes: a storing unit that temporally stores the imaging signal read out by the driving unit from the plurality of pixels, and a transmitting unit that reads out the imaging signal stored in the storing unit and transmits the read-out imaging signal to a control device which processes the imaging signal to generate image data, and the transmitting unit transmits the imaging signal at a constant transmitting speed regardless of the read-out speed of the imaging signal.

8. The electronic endoscopic device of claim 1, wherein the endoscopic scope includes: a storing unit that temporally stores the imaging signal read out by the driving unit from the plurality of pixels, and a transmitting unit that reads out the imaging signal stored in the storing unit and transmits the read-out imaging signal to a control device which processes the imaging signal to generate image data, and the transmitting unit transmits the imaging signal at a constant transmitting speed regardless of the read-out speed of the imaging signal.

* * * * *